US006277386B1

(12) United States Patent
Kim et al.

(10) Patent No.: US 6,277,386 B1
(45) Date of Patent: Aug. 21, 2001

(54) COSMETIC

(75) Inventors: Son Nguyen Kim, Hemsbach; Axel Sanner, Frankenthal; Wilma M Dausch, Limburgerhof; Volker Schehlmann, Römerberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/255,005

(22) Filed: Feb. 22, 1999

(30) Foreign Application Priority Data

Feb. 25, 1998 (DE) .............................. 198 07 908

(51) Int. Cl.[7] .............................. A61K 7/06; A61K 7/11; A61L 9/04
(52) U.S. Cl. ..................... 424/401; 424/70.1; 424/70.12; 424/45
(58) Field of Search ........................... 424/45, 401, 70.1, 424/70.11, 70.12

(56) References Cited

U.S. PATENT DOCUMENTS

| | | |
|---|---|---|
| 3,836,537 | 9/1974 | Boerwinkle et al. ................. 260/29 |
| 4,743,673 | 5/1988 | Johnston et al. ........................ 528/60 |
| 4,764,553 * | 8/1988 | Mosbach et al. ..................... 524/591 |
| 4,814,101 | 3/1989 | Schieferstein ........................ 252/174 |
| 5,306,484 | 4/1994 | Potthoff-karl ........................... 424/47 |
| 5,643,581 | 7/1997 | Mougin et al. ....................... 424/401 |
| 5,968,494 * | 10/1999 | Kukkala et al. ..................... 424/70.1 |
| 6,007,793 * | 12/1999 | Bhatt et al. ............................. 424/47 |

FOREIGN PATENT DOCUMENTS

| | | |
|---|---|---|
| 2066226 | 3/1991 | (CA) . |
| 4225045 | 7/1992 | (DE) . |
| 4241118 | 12/1992 | (DE) . |
| 4314305 | 4/1993 | (DE) . |
| 19541326 | 11/1995 | (DE) . |
| 19541329 | 11/1995 | (DE) . |
| 017122 | 3/1979 | (EP) . |
| 362860 | 4/1990 | (EP) . |
| 408311 | 1/1991 | (EP) . |
| 412704 | 2/1991 | (EP) . |
| 619111 | 10/1994 | (EP) . |
| 729742 | 9/1996 | (EP) . |
| 1596875 | 9/1981 | (GB) . |
| 93/03703 | 3/1993 | (WO) . |
| 97/17052 | 5/1997 | (WO) . |
| 97/17386 | 5/1997 | (WO) . |
| 97/25021 | 7/1997 | (WO) . |

\* cited by examiner

*Primary Examiner*—Thurman K. Page
*Assistant Examiner*—S. Howard
(74) *Attorney, Agent, or Firm*—Keil & Weinkauf

(57) ABSTRACT

A cosmetic or pharmaceutical composition which comprises at least one water-soluble or water-dispersible polyurethane of a) at least one polymer having two active hydrogen atoms per molecule which is selected from polytetrahydrofurans, polysiloxanes and mixtures thereof, b) at least one polyesterdiol, c) at least one compound comprising two active hydrogens per molecule and having a molecular weight of 56–300, d) at least one compound which contains two active hydrogen atoms and at least one anionogenic or anionic group per molecule, e) at least one diisocyanate, or a salt thereof, said polyurethane not comprising any unit which originates from a primary or secondary amine having an ionogenic or ionic group.

16 Claims, No Drawings

COSMETIC

The present invention relates to a cosmetic composition which comprises at least one water-soluble or water-dispersible polyurethane based on polytetrahydrofurans, polysiloxanes and mixtures thereof and also comprises at least one polyesterdiol.

In cosmetology, polymers with film-forming properties are used for setting, shaping and improving the structure of the hair. These hair treatment compositions generally include a solution of the film former in an alcohol or in a mixture of alcohol and water.

Hairsetting compositions are generally sprayed on the hair in the form of aqueous-alcoholic solutions. Following the evaporation of the solvent, the individual hairs are held in the desired shape at their points of mutual contact by the polymer which is left behind. The polymers should on the one hand be sufficiently hydrophilic that they can be washed out of the hair, yet on the other hand should be hydrophobic so that the hair treated with the polymers retains its shape even under conditions of high atmospheric humidity, and the individual hairs do not stick to one another. In order to obtain a highly efficient hairsetting effect, moreover, it is also desirable to employ polymers which have a relatively high molecular weight and a relatively high glass temperature (at least 15° C.).

A further consideration when formulating hairsetting agents is that because of the environmental regulations governing the emission of volatile organic compounds (VOCs) into the atmosphere it is necessary to reduce the content of alcohol and of propellant.

A further current demand on hair treatment compositions is that they should give the hair a natural appearance and luster even, for example, when the hair concerned is by its very nature particularly vigorous and/or dark.

DE-A-39 01 325 and DE-A-43 14 305 describe hairsetting compositions comprising as film former copolymers based on A) t-butyl acrylate and/or t-butyl methacrylate, B) acrylic acid and/or methacrylic acid and C) a further free-radically copolymerizable monomer, all or some of the carboxyl groups of the copolymers being in neutralized form. Hairsetting agents based on such copolymers which include carboxyl-containing monomers do indeed generally have satisfactory properties in respect of the setting achieved, the elasticity and the ease of washout from the hair; however, the feel of the styles set with these polymers is perceived as unpleasantly dull and unnatural. An attempt to reduce this effect by adding customary softeners does not in general lead to satisfactory results. Consequently, an improvement in feel is generally achieved at the expense of a reduced setting effect.

It is known to employ polysiloxanes, such as polydimethylsiloxane, and polysiloxane derivatives in haircare compositions.

EP-A-017 122 describes the use of polysiloxane-ammonium derivatives in hair washing and hair treatment compositions for improving the combability, softness and body of the hair.

EP-A-729 742 describes hair treatment compositions based on A) an amino-modified silicone terpolymer and B) at least one cationic, silicone-free conditioning agent based on a quaternary ammonium salt.

A disadvantage of the use, described in the two above-mentioned publications, of polysiloxanes which are not bonded covalently to the setting polymer is that there are frequent instances of separation of the formulations in the course of storage and following their application to the hair.

EP-A-408 311 describes the use of copolymers comprising units of a) ethylenically unsaturated, hydrophilic monomers and b) ethylenically unsaturated monomers with polysiloxane groups in haircare products.

EP-A-412 704 describes a haircare composition based on a graft copolymer which has monovalent siloxane polymer units on a backbone which is based on a vinyl polymer. After drying, the polymer breaks down into a discontinuous, silicone-containing phase and a continuous, silicone-free phase.

WO 93/03703 describes a hairspray composition comprising: a) 0.1 to 2% by weight of a surface-active agent, b) from 0.5 to 15% by weight of an ionic resin having an number-average molecular weight of at least 300,000 and c) a liquid vehicle. In this case the ionic resin comprises silicone-containing monomers and, after drying, breaks down into a discontinuous, silicone-containing phase and a silicone-free continuous phase.

EP-A-362 860 describes alcohol-modified silicone ester derivatives and cosmetic compositions comprising them.

None of these publications describes setting polymers based on polyurethanes having a covalent bond of the siloxane groups to the setting polymers via nitrogen-containing groups. One disadvantage of the above-mentioned siloxane-containing polymers is the complex synthesis of the constituent monomers. In addition, unreacted macromonomers and nonpolymerizable impurities arising from the preparation, owing to their high molecular weight, are very difficult if not impossible to separate from the siloxane-containing setting polymers. These components, however, are generally not entirely free from toxicological and allergological concerns. In addition, the suitability of such polymers for producing low-VOC formulations is extremely limited. Owing to their film-forming properties and generally low viscosity in water/ethanol, it is known to employ polyesters, polyamides or polyurethanes which are dispersible or soluble in water in cosmetics. For instance, U.S. Pat. No. 4,743,673 describes hydrophilic polyurethane polymers with carboxyl groups in the polymer backbone. These polyurethanes are synthesized from a polyol component, which can be an alkylene glycol, a polyoxyalkylene glycol or a linear polyesterdiol, a carboxylic ester component having hydroxyl or amino groups, and an organic isocyanante or isocyanate precursor. Thus the polyurethane contains, attached to the polymer backbone, ester groups which are subsequently hydrolyzed by from 30 to 60 minutes of refluxing with a strong base such as sodium or potassium hydroxide. The resulting product no longer gives a clear solution either in water or in ethanol. Especially when the polyol component used is a polyesterdiol, treatment with the strong base under reflux conditions causes hydrolysis not only of the ester groups of the carboxylic ester component but also of those in the polyurethane chain. As a result, the polyurethane chain is cleaved and there is a drastic reduction in the molecular weight of the polyurethane. Admittedly, there is a mention of the use of the polyurethanes in hairsprays, although in practice the films obtained with these polyurethanes cannot be used for hair cosmetics since they are either insoluble in water or have too low a molecular weight and hence an inadequate setting effect.

DE-A-42 25 045 describes the use of water-soluble or water-dispersible anionic polyurethanes as hairsetting agents. These polyurethanes are synthesized from
a) at least one compound containing two or more active hydrogen atoms per molecule, b) at least one diol which contains acid groups or salt groups, and
c) at least one diisocyanate.

They possess a glass temperature of at least 15° C. and an acid number of from 12 to 150. Polyurethanes based on polytetrahydrofurans and/or polysiloxanes are not described. In terms of their elasticity, hairsetting polymers based on these polyurethanes are in need of improvement and generally lack a pleasant feel.

DE-A-42 41 118 describes the use of cationic polyurethanes and polyureas as auxiliaries in cosmetic and pharmaceutical formulations. They are employed in particular as film formers in hairsetting compositions, and are synthesized from
a) at least one diisocyanate which may have already been reacted beforehand with one or more compounds containing two or more active hydrogen atoms per molecule, and
b) at least one diol, primary or secondary amino alcohol, primary or secondary diamine or primary or secondary triamine having one or more tertiary, quaternary or protonated tertiary amine nitrogen atoms.

The polymers have a glass transition temperature of at least 25° C. and an amine number of from 50 to 200, based on the nonquaternized or protonated compounds. Polyurethanes with cationic groups form hygroscopic films, which are tacky. In general, therefore, they do not meet the requirements in terms of gloss and natural appearance that are currently imposed on hairsetting polymers.

EP-A-619 111 describes the use of polyurethanes based on organic diisocyanates, diols and 2,2-hydroxymethyl-substituted carboxylates of the formula

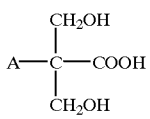

where A is a hydrogen atom or a $C_1$–$C_{20}$-alkyl group in hairfixatives. In this case at least some of the carboxyl groups are neutralized with an organic or inorganic base. The diols have a molecular weight in the range from 300 to 20,000, polytetrahydrofurans being among the suitable diol components mentioned. None of the working examples, however, describes a polyurethane based on a polytetrahydrofuran. Polyurethanes comprising in copolymerized form a polymeric diol, a polyesterdiol and a compound of low molecular mass having two active hydrogen atoms are not described. Similarly, polysiloxane-based polyurethanes are not described either. Films based on the above polyurethanes are soft and tacky, and the hairsetting compositions based thereon, correspondingly, are in need of improvement.

The polyurethanes described in the latter publications can go only part-way toward meeting the requirements made of hairsetting polymers. For instance, with all of the above-mentioned polyurethane-based products the desired sleekness of the hair is in need of improvement.

EP-A-636 361 describes a cosmetic composition comprising, in a cosmetically compatible vehicle, at least one pseudolatex based on a polycondensate which comprises at least one polysiloxane unit and at least one polyurethane and/or polyurea unit having anionic or cationic groups. The anionic groups comprise fully or partly neutralized carboxyl or sulfo groups; the cationic groups are fully or partly neutralized and/or quaternized tertiary amines. There is no description of polyurethanes based on polytetrahydrofurans and/or polysiloxanes, polyesterdiols and a low molecular mass compound having two active hydrogen atoms. The disclosure content of WO 97/25021 is similar. These cosmetic compositions are suitable, inter alia, for treating keratinous materials. The ease of washout of these film formers, however, is unsatisfactory. In addition, their high siloxane content robs them of the setting effect also required of a hair polymer.

DE-A-195 41 329 and WO 97/17052 describe hair treatment compositions comprising a salt which is dispersible or soluble in water and has the formula I $$[A-(X)_n]^{n-} \cdot [H_m B]^{m+} \qquad I$$

where
A is a cosmetically acceptable aliphatic, cycloaliphatic or aromatic radical, which may have siloxane-containing units and/or fluorine-containing units,
X is a carboxylate, sulfonate, phosphate or phosphonate group;
B is a cosmetically acceptable amine base which may comprise siloxane-containing and/or fluorine-containing units;
n is from 1 to 30; and
m is the valence of the amine B.

Hairspray formulations based on these siloxane-containing salts, on a hairsetting polymer which does not contain siloxane and on a silicone oil lead to films which are easily removed from the surface of the hair by mechanical stress, for example. The setting effect of these formulations is therefore in need of improvement.

DE-A-195 41 326 and WO 97/17386 describe water-soluble or water-dispersible polyurethanes having terminal acid groups, their preparation and their use. In this case a polyurethane prepolymer which is dispersible or soluble in water and has terminal isocyanate groups is reacted with an aminosulfonic or aminocarboxylic acid, especially taurine, aspartic acid and glutamic acid. Hairsprays based on these polyurethanes are still in need of improvement. For instance, the aminocarboxylates and aminosulfonates employed have to be prepared freshly in each case from the corresponding acids by neutralization. Problems may occur in particular when formulating hairsprays having a high content of propellant gas and/or a high content of organic solvents and, if appropriate, with the simultaneous use of spray atomizers for obtaining very small droplets.

It is an object of the present invention to provide new cosmetic compositions, especially polyurethane-based hair treatment compositions, which firstly can be used as hairsetting compositions and secondly possess great ease of washout (redispersibility). They should impart smoothness and sleekness to the hair.

We have found that this object is achieved by means of water-soluble and/or water-dispersible polyurethanes which comprise at least one polytetrahydrofuran, a polysiloxane or a mixture thereof and at least one polyesterdiol.

The present invention therefore relates to an aqueous cosmetic composition comprising at least one water-soluble or water-dispersible polyurethane of
a) at least one polymer having two active hydrogen atoms per molecule which is selected from polytetrahydrofurans, polysiloxanes and mixtures thereof,
b) at least one polyesterdiol,
c) at least one compound having a molecular weight in the range from 56 to 300 which contains two active hydrogen atoms per molecule,
d) at least one compound which contains two active hydrogen atoms and at least one anionogenic or anionic group per molecule,
e) at least one diisocyanate, or a salt thereof, said polyurethane not comprising any unit which originates from a primary or secondary amine having an ionogenic or ionic group.

Component a) is preferably a polymer having a number-average molecular weight in the range from about 400 to 4000, preferably from 500 to 4000 and, in particular, from 600 to 3000. Suitable polytetrahydrofurans can be prepared by cationic polymerization of tetrahydrofuran in the presence of acidic catalysts such as sulfuric or fluorosulfuric acid, for example. Preparation techniques of this kind are known to the skilled worker.

The polysiloxanes a) preferably comprise a compound of the formula I

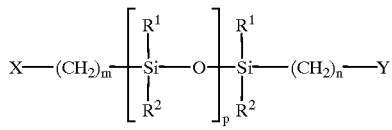

where
$R^1$ and $R^2$ independently of one another are $C_1$- to $C_4$-alkyl, benzyl or phenyl,
X and Y independently of one another are OH or $NHR^3$, where $R^3$ is hydrogen, $C_1$- to $C_6$-alkyl or $C_5$- to $C_8$-cycloalkyl,
m and n independently of one another are from 2 to 8, and p is from 3 to 50.

Examples of suitable alkyl radicals are methyl, ethyl, n-propyl, isopropyl, n-butyl, t-butyl, n-pentyl, n-hexyl etc. Examples of suitable cycloalkyl radicals are cyclopentyl, cyclohexyl, cycloheptyl, cyclooctyl, etc.

$R^1$ and $R^2$ are preferably both methyl.

Suitable polyesterdiols b) have a number-average molecular weight in the range from about 400 to 5000, preferably from 500 to 3000 and, in particular, from 600 to 2000.

Suitable polyesterdiols are all those which are normally employed to prepare polyurethanes, especially those based on aromatic dicarboxylic acids, such as terephthalic, isophthalic, phthalic, Na- or K-sulfoisophthalic acid, etc., on aliphatic dicarboxylic acids, such as adipic or succinic acid, etc., and on cycloaliphatic dicarboxylic acids, such as 1,2-, 1,3- or 1,4-cyclohexanedicarboxylic acid. Particularly suitable diols are aliphatic diols, such as ethylene glycol, propylene glycol, 1,6-hexanediol, neopentyl glycol, diethylene glycol, polyethylene glycols, polypropylene glycols, 1,4-dimethylolcyclohexane, and also poly(meth)acrylatediols of the formula

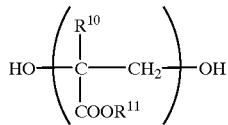

where $R^{10}$ is H or $CH_3$ and $R^{11}$ is $C_1$–$C_{18}$-alkyl (especially $C_1$–$C_{12}$- or $C_1$–$C_8$-alkyl) and which have a molecular mass of up to about 3000. Diols of this kind can be prepared by conventional means and are obtainable commercially (Tegomer® grades MD, BD and OD from Goldschmidt).

Preference is given to polyesterdiols based on aromatic and aliphatic dicarboxylic acids and aliphatic diols, especially those in which the aromatic dicarboxylic acid accounts for from 10 to 95 mol-%, in particular from 40 to 90 mol-% and, preferably, from 50 to 85 mol-% of the overall dicarboxylic acid component (the remainder being aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-NaSO$_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolcyclohexane, and 5-NaSO$_3$-isophthalic acid/isophthalic acid/adipic acid/neopentyl glycol/diethylene glycol/dimethylolcyclohexane.

Component c) preferably comprises diols, diamines, amino alcohols, and mixtures thereof. The molecular weight of these compounds is preferably within a range from about 56 to 280. If desired up to 3 mol-% of the mentioned compounds can be replaced by triols or triamines. In this case the resulting polyurethanes are essentially uncrosslinked.

As component c) it is preferred to employ diols. Examples of diols which can be used are ethylene glycol, propylene glycol, butylene glycol, neopentyl glycol, cyclohexanedimethylol, di-, tri-, tetra-, penta- or hexaethylene glycol and mixtures thereof. It is preferred to employ neopentyl glycol and/or cyclohexanedimethylol.

Examples of suitable amino alcohols are 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol etc.

Examples of suitable diamines are ethylenediamine, propylenediamine, 1,4-diaminobutane, 1,5-diaminopentane and 1,6-diaminohexane, and also α,ω-diamino polyethers, which can be prepared by aminating polyalkylene oxides with ammonia.

Suitable compounds d), which contain two active hydrogen atoms and at least one anionogenic or anionic group per molecule, are, for example, compounds having carboxylate and/or sulfonate groups. Particular preference is given as component d) to dimethylolpropanoic acid and mixtures comprising it.

As component d) it is also possible to use compounds of the formulae

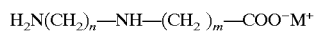
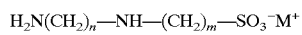

where m and n independently of one another are an integer from 1 to 8, in particular from 1 to 6, and M is Li, Na or K. Preference is given to employing as component d) mixtures comprising dimethylolpropanoic acid and up to 3% by weight, based on the overall amount of components a) to e), of at least one compound of the above formulae.

Component e) comprises customary aliphatic, cycloaliphatic and/or aromatic diisocyanates, such as tetramethylene diisocyanate, hexamethylene diisocyanate, methylenediphenyl diisocyanate, 2,4-and 2,6-tolylene diisocyanate and isomer mixtures thereof, 1,5-naphthylene diisocyanate, 1,4-cyclohexylene diisocyanate, dicyclohexylmethane diisocyanate and mixtures thereof, especially isophorone diisocyanate and/or dicyclohexylmethane diisocyanate. If desired, up to 3 mol-% of these compounds may be replaced by triisocyanates.

The compositions according to the invention preferably comprise at least one polyurethane of
from 0.5 to 40% by weight, preferably from 2 to 30% by weight, of at least one component a),
from 1 to 45% by weight, preferably from 2 to 35% by weight, of at least one polyesterdiol b),
from 0.3 to 15% by weight, preferably from 0.5 to 12% by weight, of at least one component c), from 5 to 25% by weight, preferably from 8 to 20% by weight, of at least one component d), from 25 to 60% by weight, preferably from 35 to 53% by weight, of at least one component e).

In a preferred embodiment the compositions of the invention comprise at least one polyurethane which as its component a) comprises, in copolymerized form, essentially or exclusively, one or more tetrahydrofurans. In this case the polyurethane preferably comprises from 5 to 40% by weight, preferably from 10 to 35% by weight, of at least one polytetrahydrofuran a), from 1 to 40% by weight, preferably from 2 to 30% by weight, of at least one polyesterdiol b), from 0.3 to 15% by weight, preferably from 0.5 to 12% by weight, of at least one component c), from 5 to 25% by weight, preferably from 8 to 20% by weight, of at least one component d), from 25 to 60% by weight, preferably from 35 to 53% by weight, of at least one component e), where the polytetrahydrofuran a) can be replaced in a proportion of up to about 8% by weight, preferably 5% by weight, based on the overall amount of components a) to e), by a polysiloxane.

In a further preferred embodiment the compositions of the invention comprise at least one polyurethane which as its component a) comprises, in copolymerized form, essentially or exclusively, one or more polysiloxanes. In this case the polyurethane preferably comprises from 0.2 to 20% by weight, preferably from 0.5 to 15% by weight, in particular from 1 to 10% by weight, of at least one polysiloxane a), from 10 to 45% by weight, preferably from 15 to 40% by weight, of at least one polyesterdiol b), from 0.3 to 15% by weight, preferably from 0.5 to 12% by weight, of at least one component C), from 5 to 25% by weight, preferably from 8 to 20% by weight, of at least one component d), from 25 to 60% by weight, preferably from 35 to 53% by weight, of at least one component e).

If desired, some of the polyesterdiol b) can be replaced by an equimolar amount of a polytetrahydrofuran a).

The polyurethanes employed in the compositions of the invention are prepared by reacting the compounds of components a), b), c) and d) with component e). In this reaction the temperature is within a range from 60 to 140° C., preferably from about 70 to 100° C. The reaction can take place without solvent or in a suitable inert solvent or solvent mixture. Suitable solvents are aprotic polar solvents, examples being tetrahydrofuran, ethyl acetate, N-methylpyrrolidone, dimethylformamide and, preferably, ketones, such as acetone and methyl ethyl ketone. The reaction preferably takes place under an inert gas atmosphere, such as under nitrogen, for example. The components are employed in amounts such that the ratio of NCO equivalent of the compounds of component a) to equivalent of active hydrogen atom of components a), b), c) and d) is within a range from about 0.8:1 to 1.25:1, preferably from 0.85:1 to 1.2:1 and, in particular, from 1.05:1 to 1.15:1. If the resulting polyurethanes still have free isocyanate groups, these are finally deactivated by adding amines, preferably amino alcohols. Suitable amino alcohols are those described above as component c), preferably 2-amino-2-methyl-1-propanol.

The polyurethanes which contain acid groups can be converted by full or partial neutralization with a base into a water-soluble or water-dispersible form.

As a general rule, the resulting salts of the polyurethanes are more water-soluble or dispersible in water than the non-neutralized polyurethanes. The base used to neutralize the polyurethanes can comprise alkali metal bases, such as sodium hydroxide, potassium hydroxide, sodium carbonate, sodium hydrogen carbonate, potassium carbonate or potassium hydrogen carbonate, and alkaline earth metal bases, such as calcium hydroxide, calcium oxide, magnesium hydroxide or magnesium carbonate, and also ammonia and amines. Examples of suitable amines are $C_1$–$C_6$-alkylamines, preferably n-propylamine and n-butylamine, dialkylamines, preferably diethylpropylamine and dipropylmethylamine, trialkylamines, preferably triethylamine and triisopropylamine, $C_1$–$C_6$-alkyldiethanolamines, preferably methyl- or ethyldiethanolamine, and di-$C_1$–$C_6$-alkylethanolamines. Bases which have proven particularly suitable for use in hair treatment compositions for neutralizing the polyurethanes which contain acid groups are 2-amino-2-methyl-1-propanol, diethylaminopropylamine and triisopropanolamine. Neutralization of the polyurethanes which contain acid groups can also be performed with the aid of mixtures of two or more bases, such as mixtures of sodium hydroxide and triisopropanolamine, for example. Depending on the end use, neutralization can be carried out partially, to the extent of from 20 to 40%, for example, or completely, i.e. 100%.

Where a water-miscible organic solvent is used in preparing the polyurethanes it can be removed subsequently by customary techniques known to the skilled worker, such as by distillation under reduced pressure. In addition, water can be added to the polyurethane before the solvent is separated off. Replacing the solvent by water gives a solution or dispersion of the polymer from which, if desired, the polymer can be obtained in a customary manner—for example, by spray drying.

The polyurethanes employed in the compositions of the invention have K values (measured in accordance with E. Fikentscher, Cellulose-Chemie 13 (1932), 58–64, on a 1% strength solution in N-methylpyrrolidone) in a range from 15 to 90, preferably from 20 to 60. Their glass transition temperature is generally at least 45° C., preferably at least 20° C., with particular preference at least 25° C. and, especially, at least 30° C. Where the compositions of the invention comprise polyurethanes having units derived from polysiloxanes of the formula I, the proportion of siloxane groups, based on the solids content of the polyurethanes of the invention, is generally from about 0.05 to 20% by weight, preferably from about 0.05 to 15% by weight and, in particular, from 0.05 to 10% by weight. Compositions comprising at least one polyurethane having a siloxane content in the range from about 5 to 20% by weight, preferably from 7 to 17% by weight, are of preferential suitability as solubilizers for hydrophobic products, especially silicones, and as additives for hair treatment compositions.

The cosmetic compositions of the invention are particularly suitable as compositions for coating keratinous surfaces (hair, skin and nails). Where the compounds employed in the compositions of the invention are dispersible in water, they can be applied in the form of aqueous microdispersions having particle diameters of usually from 1 to 150 nm, preferably from 5 to 100 nm. In this case the solids contents of the preparations are usually within a range from about 0.5 to 20% by weight, preferably from 1 to 12% by weight. In general, such microdispersions do not require stabilization by emulsifiers or surfactants.

With preference, the compositions of the invention can be in the form of a hair treatment composition, especially in the form of a hairspray. For use as hair setting agents, preferred compositions are those comprising polyurethanes whose glass transition temperature $T_g \geq 20°$ C., preferably $\geq 30°$ C. The K value of these polymers is preferably within a range from 23 to 90, in particular from 25 to 60. Where polyurethanes are employed in compositions for use as hairsetting products and where these polyurethanes contain units derived from polysiloxanes, the proportion of siloxane groups, based on the solids content, is generally not more than 15% by weight.

In general, the compositions of the invention comprise the polyurethanes in an amount in the range from 0.2 to 20% by weight, based on the overall weight of the composition.

The compositions are preferably hair treatment compositions, and are usually in the form of an aqueous dispersion or in the form of an alcoholic or aqueous-alcoholic solution. Examples of suitable alcohols are ethanol, propanol, isopropanol, etc.

In addition, the hair treatment compositions of the invention generally include customary cosmetic auxiliaries, examples being softeners, such as glycerol and glycol; emollients; perfumes; UV absorbers; colorants; thickeners; antistatic substances; combability improvers; preservatives; and foam stabilizers.

When formulated as hairsprays, the novel compositions comprise a sufficient amount of a propellant: for example, a low-boiling hydrocarbon or ether, such as propane, butane, isobutane or dimethyl ether. As propellants it is also possible to use compressed gasses, such as nitrogen, air or carbon dioxide. The amount of propellant can be kept low so as not unnecessarily to raise the VOC content. In general the said amount is not more than 55% by weight, based on the overall weight of the composition. However, higher VOC contents of 85% by weight or more are also possible if desired.

The polyurethanes described above can also be employed in the compositions in combination with other hair polymers. Such polymers are, in particular:

nonionic, water-soluble or water-dispersible polymers or oligomers, such as polyvinylcaprolactam, e.g. Luviskol Plus (BASF), or polyvinylpyrrolidone and its copolymers, especially with vinyl esters such as vinyl acetate, e.g. Luviskol VA 37 (BASF); polyamides, for example those based on itaconic acid and aliphatic diamines;

amphoteric or zwitterionic polymers, such as the octylacrylamide/methyl methacrylate/tert-butylamionoethyl methacrylate/2-hydroxypropyl methacrylate copolymers obtainable under the designations Amphomer® (Delft National), and zwitterionic polymers as disclosed, for example, in German Patent Applications DE 39 29 973, DE 21 50 557, DE 28 17 369 and DE 37 08 451. Acrylamido-propyltrimethylammonium chloride/ acrylic acid and/or methacrylic acid copolymers, and the alkali metal salts and ammonium salts thereof, are preferred zwitterionic polymers. Suitable zwitterionic polymers are also methacryloylethyl betaine/methacrylate copolymers, which are obtainable commercially under the designation Amersette® (AMERCHOL);

anionic polymers, such as vinyl acetate/crotonic acid copolymers, as are commercially available, for example, under the designation Resyn® (NATIONAL STARCH), Luviset® (BASF) and Gafset® (GAF), vinylpyrrolidone/ vinyl acrylate copolymers, obtainable for example under the trademark Luviflex® (BASF). A preferred polymer is the vinylpyrrolidone/acrylate terpolymer obtainable under the designation Luviflex® VBM-35 (BASF), acrylic acid/ethyl acrylate/N-tert-butylacrylamide terpolymers, which are marketed, for example, under the designation Ultrahold® strong (BASF), and Luvimer® (BASF, terpolymer of t-butyl acrylate, ethyl acrylate and methacrylic acid), or cationic (quaternized) polymers, e.g. cationic polyacrylate copolymers based on N-vinyllactams and derivatives thereof (N-vinylpyrrolidone, N-vinylcaprolactam etc.) and also customary cationic hair conditioner polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers formed by reacting polyvinylpyrrolidone with quaternary ammonium compounds), Polymer JR (hydroxyethylcellulose with cationic groups), polyquaternium types (CTFA names) etc.;

nonionic, siloxane-containing, water-soluble or -dispersible polymers, e.g. polyether siloxanes, such as Tegopren® (Goldschmidt) or Belsil® (Wacker).

The above-described polyurethanes based on at least one polytetrahydrofuran and/or polysiloxane and at least one polyesterdiol are preferably employed as a mixture with another amido-functional hair polymer. Such polymers include, for example, the polyurethanes described in DE-A-42 25 045, the above-described vinylpyrrolidone/acrylate terpolymers and acrylic acid/ethyl acrylate/N-tert-butylacrylamide terpolymers (e.g. Ultraholdistrong from BASF AG), the above-described amido-functional amphoteric polymers (e.g. Amphomer®) and, in particular, copolymers having a content of amido-functional monomers, such as N-vinyllactams, of at least 30% by weight (e.g. Luviskol®plus and Luviskol®VA37 from BASF AG). Particular preference is given to mixtures of the above-described siloxane-functional, polyesterdiol-containing polyurethanes with these amido-functional hair polymers.

The other hair polymers are preferably present in amounts of up to 10% by weight, based on the overall weight of the composition.

A preferred hair treatment composition comprises:
a) from 0.5 to 20% by weight of at least one polyurethane which is dispersible or soluble in water and is based on polytetrahydrofurans and/or polysiloxanes and on polyesterdiols,
b) from 40 to 99% by weight, preferably from 50 to 98% by weight, of a solvent selected from water and water-miscible solvents, preferably $C_2$- to $C_5$ alcohols, especially ethanol, and mixtures thereof,
c) from 0 to 50% by weight of a propellant, preferably dimethyl ether,
d) from 0 to 15% by weight of at least one hair polymer which is different from a) and is dispersible or soluble in water,
e) from 0 to 0.2% by weight of at least one water-insoluble silicone,
f) from 0 to 2% by weight of at least one nonionic, siloxane-containing polymer which is dispersible or soluble in water.

The composition of the invention may include as component d) at least one other hair polymer which is dispersible or soluble in water. The proportion of this component will then in general be from about 0.1 to 15% by weight, preferably from 0.1 to 10% by weight, based on the overall weight of the composition. In this context it is possible with preference to employ water-soluble or water-dispersible polyurethanes which contain no siloxane groups in copolymerized form.

The composition of the invention may as component e) comprise at least one water-insoluble silicone, especially a polydimethylsiloxane, e.g. the Abil® grades from Goldschmidt. The proportion of this component will then in general be from about 0.001 to 0.2% by weight, preferably from 0.01 to 0.1% by weight, based on the overall weight of the composition.

The composition of the invention may as component f) comprise at least one nonionic, siloxane-containing, water-soluble or dispersible polymer, selected in particular from the polyether siloxanes described above. The proportion of this component will then in general be from about 0.001 to 2% by weight, based on the overall weight of the composition.

The composition of the invention may additionally comprise, if desired, an antifoam based, for example, on silicone. The amount of the antifoam will then in general be up to about 0.001% per weight, based on the overall amount of the composition.

A particularly preferred hair treatment composition comprises:

a) from 0.5 to 20% by weight of at least one polyurethane which is dispersible or soluble in water and is based on polysiloxanes,
b) from 50 to 98% by weight of a solvent selected from water, ethanol and mixtures thereof,
c) from 0 to 50% by weight of a propellant,
d) from 0.1 to 10% by weight of at least one amido-functional, silicone-free hair polymer which is dispersible or soluble in water,
e) from 0 to 0.1% by weight of at least one water-insoluble silicone,
f) from 0 to 1% by weight of at least one nonionic, siloxane-containing polymer which is dispersible or soluble in water, and customary additives.

In one preferred embodiment the amido-functional hair polymer d) is a polymer which comprises, in copolymerized form, one or more amido-containing monomers. Preferred amido-containing monomers are N-vinyllactams, which are preferably selected from N-vinylpyrrolidone, N-vinylcaprolactam, derivatives thereof, which may for example contain one or more $C_1$- to $C_4$-alkyl substituents, and mixtures of these. The hair polymers d) then comprise these monomers, in copolymerized form, preferably in an amount of at least 30% by weight. Also suitable is a polymer mixture which has at least one such copolymer. Particular preference is given to the Luviskol® grades from BASF AG, such as Luviskol VA37 and Luviskol plus.

In accordance with a further preferred embodiment the amido-functional hair polymer d) comprises a silicone-free polyurethane as described, for example, in DE-A-42 25 045, DE-A-42 41 118 and EP-A-619 111.

The compositions of the invention possess the advantage that on the one hand they give the hair the desired set and on the other hand the polymers are easy to wash out (redispersible) and give the hair, in addition, smoothness and/or luster. Furthermore, it is possible to formulate hair treatment compositions with a VOC content of less than 85% by weight, preferably less than 60% by weight, and also to prepare purely aqueous formulations, even if they are formulated as hairsprays.

The above-described polyurethanes based on at least one polytetrahydrofuran and/or polysiloxane are also suitable as auxiliaries in pharmacy—for example, as coating agents and/or binders for solid drug forms. They can be employed furthermore, in creams and as tablet coatings and tablet binders. They are suitable, furthermore, for use as coating compositions for the textile, paper, printing, leather and adhesives industries.

The invention is elucidated further by the following non-limiting examples.

EXAMPLES

Comparative Example 1, Novel Examples 2 to 9

Polyurethane Preparation

In an apparatus fitted with stirrer, dropping funnel, thermometer, reflux condenser and equipment for operating under nitrogen a polyesterdiol ($M_n$=1000 g/mol, prepared from isophthalic acid, adipic acid and hexanediol), a polytetrahydrofuran ($M_n$=1000 g/mol) if appropriate (Novel Examples 5 to 9), neopentyl glycol and dimethylolpropanoic acid in an amount in accordance with Table 1 were dissolved in methyl ethyl ketone (solids content of the resulting reaction solution about 75%) with heating at 70° C. and with stirring. Stirring was subsequently continued while adding isophorone diisocyanate dropwise in an amount in accordance with Table 1, during which the reaction temperature rose. At an internal temperature of 85° C. the reaction mixture was then stirred until the isocyanate group content of the mixture remained virtually constant (from about 0.5 to 0.8%). The reaction mixture was diluted to 40% by weight with acetone and cooled to room temperature with stirring. At about 30° C. a polysiloxanediamine ($M_n$=900 g/mol, Tegomer® A-Si 2122 from Goldschmidt, in the form of an 80% strength solution in methyl ethyl ketone) was added if appropriate (Examples 2 to 4, 6, 7 and 9) in an amount in accordance with Table 1 to the polyurethane prepolymer prepared as described above. The mixture was reacted for a further 30 minutes, and then the remaining isocyanate groups were deactivated by adding 2-amino-2-methylpropanol. For this purpose the reaction mixture was stirred at about 400C until the isocyanate group content of the mixture was essentially 0. Subsequently, water was added to the reaction mixture, and the reaction product was neutralized with 2-amino-2-methylpropanol (pH about 8.0). The methyl ethyl ketone was then distilled off in vacuo at 40° C. to give an aqueous dispersion of the polyurethane.

A product in powder form can be obtained by spray drying.

TABLE 1

| Ex. No. | Polyester-diol[1] [mol] | Poly (THF)[2] [mol] | Polysiloxanedi-amine[3] [mol] | NPG[4] [mol] | DMPA[5] [mol] | IPDI[6] [mol] | Siloxane content [% by wt.] |
|---|---|---|---|---|---|---|---|
| C1 | 0.8 | — | — | 1.6 | 3.2 | 6.0 | 0 |
| 2 | 0.7 | — | 0.1 | 1.6 | 3.2 | 6.0 | 3.3 |
| 3 | 0.6 | — | 0.2 | 1.6 | 3.2 | 6.0 | 6.65 |
| 4 | 0.3 | — | 0.5 | 1.6 | 3.2 | 6.0 | 16.8 |
| 5 | 0.4 | 0.4 | — | 1.6 | 3.2 | 6.0 | 0 |
| 6 | 0.4 | 0.35 | 0.05 | 1.6 | 3.2 | 6.0 | 1.65 |
| 7 | 0.4 | 0.3 | 0.1 | 1.6 | 3.2 | 6.0 | 3.3 |
| 8 | 0.2 | 0.6 | — | 1.6 | 3.2 | 6.0 | 0 |
| 9 | 0.2 | 0.55 | 0.05 | 1.6 | 3.2 | 6.0 | 1.65 |

[1]Polyesterdiol of isophthalic acid, adipic acid, hexanediol, $M_n$ = 1000 g/mol
[2]Polytetrahydrofuran, $M_n$ = 1000 g/mol
[3]Polysiloxanediamine, $M_n$ = 900 g/mol
[4]NPG = neopentyl glycol
[5]DMPA = dimethylolpropanoic acid
[6]IPDI = isophorone diisocyanate Practical Examples Examples 10 to 18

Aerosol hairspray formulations with a VOC content of 97% by weight:

| | | |
|---|---|---|
| Polyurethane of Example 1–9 | 3.0% | by weight |
| Ethanol | 62.00% | by weight |
| Dimethyl ether | 34.96% | by weight |
| Perfume, additives | q.s. | |

Examples 19 to 27

Aerosol hairspray formulations with a VOC content of 97% by weight:

| | | |
|---|---|---|
| Polyurethane of Example 1–9 | 1.50% | by weight |
| Siloxane-free, amido-functional hair polymer (Luviskol ® Plus from BASF AG) | 1.50% | by weight |
| Ethanol | 62.00% | by weight |
| Dimethyl ether | 34.96% | by weight |
| Perfume, additives | q.s. | |

Examples 28 to 36

Compact aerosol hairspray formulations with a VOC content of 90% by weight:

| | | |
|---|---|---|
| Polyurethane of Example 1–9 | 10.00% | by weight |
| Ethanol | 55.00% | by weight |
| Dimethyl ether | 34.96% | by weight |
| Perfume, additives | q.s. | |

Example 37 to 45

Hairspray formulations with a VOC content of 80% by weight:

| | | |
|---|---|---|
| Polyurethane of Example 1–9 | 5.00% | by weight |
| Ethanol | 45.00% | by weight |
| Water | 15.00% | by weight |
| Dimethyl ether | 34.96% | by weight |
| Perfume, additives | q.s. | |

Examples 46 to 54

Hairspray formulations with a VOC content of 80% by weight:

| | | |
|---|---|---|
| Polyurethane of Example 1–9 | 2.50% | by weight |
| Siloxane-free, amido-functional hair polymer (Luviskol ® Plus from BASF AG) | 2.50% | by weight |
| Water | 15.00% | by weight |
| Dimethyl ether | 34.96% | by weight |
| Perfume, additives | q.s. | |

Examples 55 to 63

Hairspray formulations with a VOC content of 55% by weight:

| | | |
|---|---|---|
| Polyurethane of Example 1–9 | 5.00% | by weight |
| Ethanol | 20.00% | by weight |
| Water | 40.00% | by weight |
| Dimethyl ether | 34.96% | by weight |
| Perfume, additives | q.s. | |

Examples 64 to 72

Pump hairspray formulations with 0 VOC content:

| | | |
|---|---|---|
| Polyurethane of Example 1–9 | 10.00% | by weight |
| Water | 89.97% | by weight |
| Perfume, additives | q.s. | |

Film Evaluation:

The above-mentioned hairspray formulations gave clear, firm films which differed in their flexibility and smoothness. The formulations based on polyurethanes of Comparative Example 1 are less flexible, and the resulting films are not smooth. The formulations based on polyurethanes of Novel Example 4 with a high siloxane content give very soft and slightly tacky films. These polyurethanes are not suitable alone as hairsetting polymers, but can be formulated as an additive, with another setting polymer, to give silicone-containing hairsprays having very good properties.

The polyurethanes from Comparative Example 1 and Novel Examples 2 to 9 were formulated individually or in the form of mixtures, with or without the addition of a water-insoluble silicone, as 5% strength by weight solutions in ethanol. The compositions of these formulations are shown in Table 3. The formulations are applied to a glass plate and the resulting films were tested for four criteria, which are indicated in Table 2, and given ratings from 1 to 4. The evaluations of the films are likewise shown in Table 3.

TABLE 2

| Evaluation criteria | | Rating |
|---|---|---|
| A) elasticity/tackiness | brittle (slightly tacky) | 4 |
| | soft (slightly tacky) | 3 |
| | hard (non-tacky) | 2 |
| | elastic (non-tacky) | 1 |
| B) Smoothness | rough | 4 |
| | moderately smooth | 3 |
| | smooth | 2 |
| | very smooth | 1 |
| C) Ease of washout | poor | 4 |
| | moderate | 3 |
| | good | 2 |
| | very good | 1 |
| D) Appearance | non-uniform, cloudy | 4 |
| | non-uniform, clear | 3 |
| | uniform, clear | 2 |
| | uniform, lustrous | 1 |

TABLE 3

Film properties of the polyurethanes

| Polymer solution[1] | Polyurethane from Preparation Example No. (% by weight) | Polydimethylsiloxane[2] [% by weight] | A | B | C | D |
|---|---|---|---|---|---|---|
| CS1 | 1 (5) | — | 2 | 2–3 | 3 | 2 |
| CS2 | 1 (5) | 0.0005 | 2 | 2 | 3–4 | 3 |
| S3 | 2 (5) | — | 2 | 1–2 | 3 | 1–2 |
| S4 | 2 (5) | 0.0005 | 2 | 1 | 3 | 1–2 |
| S5 | 3 (5) | — | 1–2 | 1 | 3–4 | 1 |
| S6 | 4 (5) | — | 3 | 1–2 | 2 | 1 |
| S7 | 5 (5) | — | 1 | 2 | 2 | 2 |
| S8 | 6 (5) | — | 1 | 1–2 | 2 | 1 |
| S9 | 6 (5) | 0.0005 | 1 | 1 | 2 | 1 |
| S10 | 8 (5) | — | 1 | 2 | 1–2 | 2 |
| S11 | 1 (3.5)/4 (1.5) | 0.0005 | 2 | 1 | 2–3 | 1 |
| S12 | 7 (3.0)/1 (2.0) | 0.0005 | 1–2 | 1 | 2 | 1 |
| S13 | 4 (4.5)/PVCap[3] (0.5) | — | 3 | 1 | 1 | 2 |
| S14 | 4 (2.5)/PVCap (2.5) | — | 1 | 1–2 | 1 | 4 |
| S15 | 4 (0.5)/PVCap (4.5) | — | 2 | 1–2 | 1 | 2 |
| S16 | 3 (2.5)/PVCap (2.5) | — | 1 | 2 | 1 | 1 |
| S17 | 7 (2.5)/PVCap (2.5) | — | 1 | 1–2 | 1 | 1 |

[1] 5% strength by weight solution in ethanol
[2] Abil ®200 from Goldschmidt
[3] PVCap = polyvinylcaprolactam

We claim:

1. A cosmetic composition comprising at least one water-soluble or water-dispersible polyurethane of
   a) at least one polymer having two active hydrogen atoms per molecule which is selected from polytetrahydrofurans, polysiloxanes and mixtures thereof,
   b) at least one polyesterdiol,
   c) at least one compound having a molecular weight in the range from 56 to 300 which contains two active hydrogen atoms per molecule,
   d) at least one compound which contains two active hydrogen atoms and at least one anionogenic or anionic group per molecule,
   e) at least one diisocyanate,
or a salt thereof, said polyurethane not comprising any unit which originates from a primary or secondary amine having an ionogenic or ionic group.

2. A composition as claimed in claim 1, where the polysiloxane
   a) is a compound of the formula I

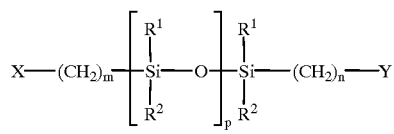

where
$R^1$ and $R^2$ independently of one another are $C_1$- to $C_4$-alkyl, benzyl or phenyl,
X and Y independently of one another are OH or $NHR^3$, where $R^3$ is hydrogen, $C_1$- to $C_6$-alkyl or $C_5$- to $C_8$-cycloalkyl, m and n independently of one another are from 2 to 8, and p is from 3 to 50.

3. A composition as claimed in claim 1, where component b) is a polyesterdiol based on an aromatic and an aliphatic dicarboxylic acid and on an aliphatic diol.

4. A composition as claimed in claim 1, where the ratio of NCO equivalent of the compounds of component e) to equivalent of active hydrogen atom of components a), b), c) and d) is within a range from 0.80:1 to 1.25:1.

5. A composition as claimed in claim 1, where free isocyanate groups of the polyurethane are deactivated by reaction with at least one amino alcohol.

6. A composition as claimed in claim 1, where anionogenic groups of component d) are fully or partly neutralized by reaction with at least one amino alcohol.

7. A composition as claimed in claim 1, comprising a polyurethane of
   from 0.5 to 40% by weight of at least one component a),
   from 1 to 45% by weight of at least one polyesterdiol b),
   from 0.3 to 15% by weight of at least one component c),
   from 5 to 25% by weight of at least one component d),
   from 25 to 60% by weight of at least one component e).

8. A composition as claimed in claim 1, comprising at least one polyurethane having a siloxane content in the range from 5 to 20% by weight as a solubilizer for hydrophobic products, especially silicones, or as an additive for hair treatment compositions.

9. A composition as claimed in claim 1, which is in the form of a hair treatment composition.

10. A composition as claimed in claim 9 comprising
    a) from 0.5 to 20% by weight of at least one polyurethane which is dispersible or soluble in water, as defined in claim 1,
    b) from 40 to 99% by weight of at least one solvent selected from water, water-miscible solvents and mixtures thereof,
    c) from 0 to 50% by weight of a propellant,
    d) from 0 to 15% by weight of at least one hair polymer which is different from a) and is dispersible or soluble in water,
    e) from 0 to 0.2% by weight of at least one water-insoluble silicone,
    f) from 0 to 2% by weight of at least one nonionic, siloxane-containing polymer which is dispersible or soluble in water.

11. A composition as claimed in claim 10, where component d) comprises at least one polymer which comprises in copolymerized form at least one amido-containing monomer in an amount of at least 30% by weight.

12. A composition as claimed in claim 10, where component d) comprises at least one polyurethane.

13. A cosmetic composition containing at least one polyurethane as defined in claim 1.

14. A pharmaceutical composition comprising at least one polyurethane as defined in claim 1 in combination with at least one pharmaceutically active ingredient.

15. Textile, paper, printing means, leather or adhesives comprising a coating composition comprising at least one polyurethane as defined in claim 1.

16. The composition defined in claim 9, which is in the form of a hairspray.

* * * * *